United States Patent [19]

Treace et al.

[11] 4,141,088

[45] Feb. 27, 1979

[54] HIP JOINT PROSTHESIS

[75] Inventors: James T. Treace, Malibu, Calif.; Dan H. Treace, Louisville, Ky.

[73] Assignee: Richards Manufacturing Company, Inc., Memphis, Tenn.

[21] Appl. No.: 812,614

[22] Filed: Jul. 5, 1977

Related U.S. Application Data

[63] Continuation of Ser. No. 768,604, Feb. 14, 1977, abandoned.

[51] Int. Cl.$^2$ ............................................. A61F 1/24
[52] U.S. Cl. ................................. 3/1.912; 128/92 C; 128/92 CA
[58] Field of Search ..................... 3/1.912, 1.913, 1.91, 3/1.911, 1.9; 128/92 C, 92 CA

[56] References Cited

U.S. PATENT DOCUMENTS

| | | | |
|---|---|---|---|
| 3,638,243 | 2/1972 | Campbell, Jr. et al. | 3/1.91 |
| 3,698,017 | 10/1972 | Scales et al. | 3/1.912 |
| 4,012,796 | 3/1977 | Weisman et al. | 3/1.913 |

OTHER PUBLICATIONS

Trapezoidal-28 Total Hip Prostheses, Zimmer (Catalog), Zimmer, USA, Warsaw, Ind. 1974 (Received Mar. 27, 1975 in PTO), pp. A14-1, A14-2, A3 and A2-1 relied upon.
A New Total Hip System Providing Alternatives and Sizes to Meet Nearly any Total Hip Reconstructive Problem. The Trapezoidal 28 from Zimmer, USA (4 Advertisement pages). The Journal of Bone & Joint Surgery, vol. 55-A, No. 3, Apr. 1973.
"The Bechtol Total Hip System", Orthopedic Catalog, Richards Mfg. Co., Inc. Memphis, Tenn. (Received Mar. 25, 1975 in PTO), pp. 1-5.

*Primary Examiner*—Ronald L. Frinks

[57] ABSTRACT

A prosthetic hip joint for use in the replacement of at least a portion of defective hip joint. The hip joint includes a femoral component and an acetabular component. The femoral component includes a stem that has an uninterrupted outer surface and is continuously tapered from the proximal end of the stem to the distal end. The stem is oval shaped in cross-section with the longer axis of the oval being in the lateral-medial plane and the shorter axis being in the anterior-posterior plane. The neck portion of the device in cross-section is narrower in its anterior-posterior dimension than its lateral-medial dimension. The femoral component is available with different length neck portions to allow the tightness of the hip joint to be varied. However, even when the length of the neck portion is varied, the distance between the center of the head and the longitudinal axis of the stem and the curvature of the stem are not varied. The acetabular component has a body of constant thickness from its socket surface to the exterior surface and there are spaced rings projecting outwardly from the exterior surface.

14 Claims, 15 Drawing Figures

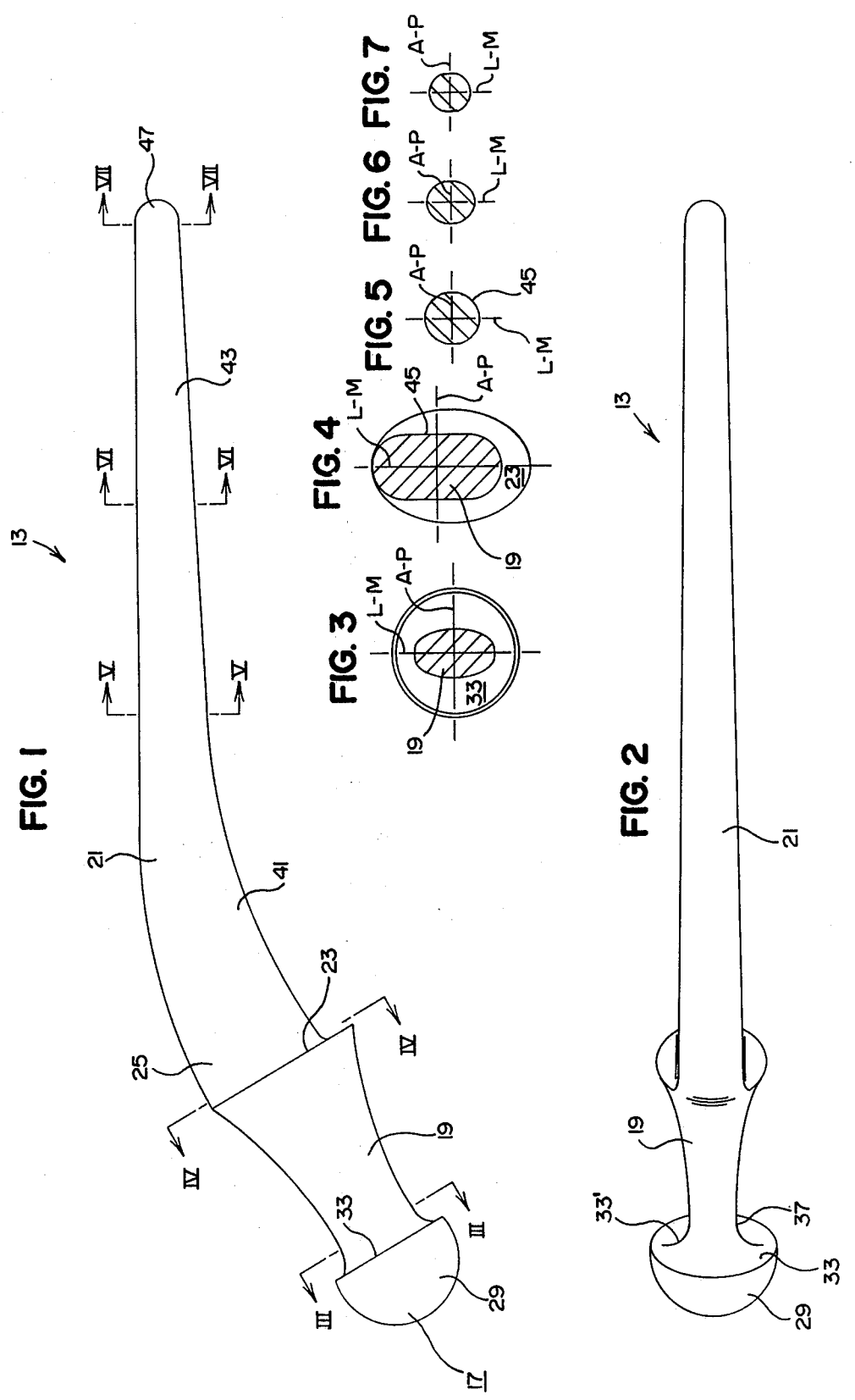

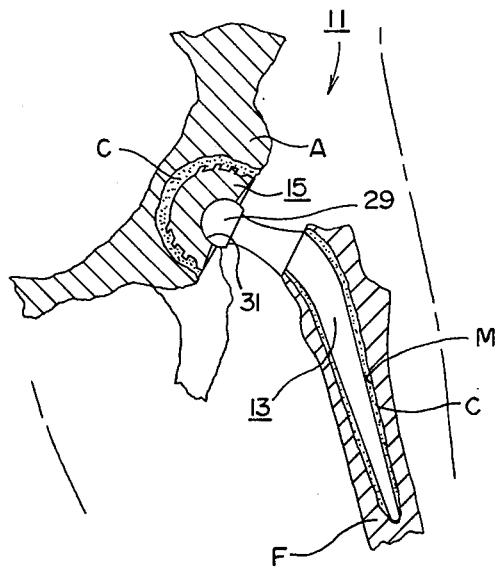
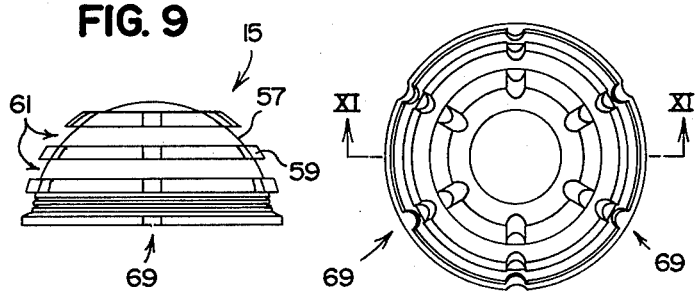
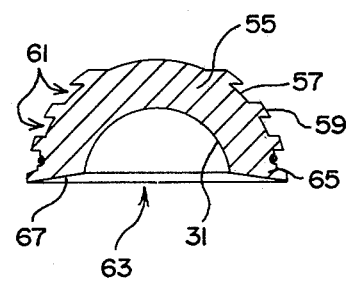
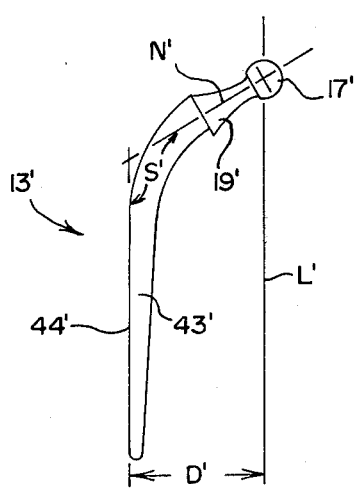
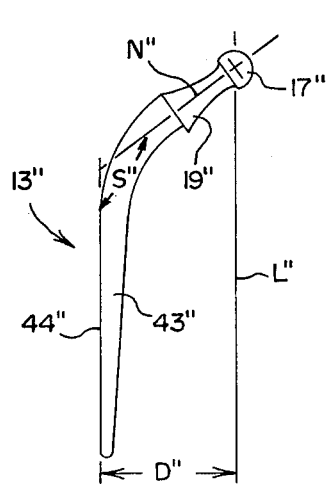
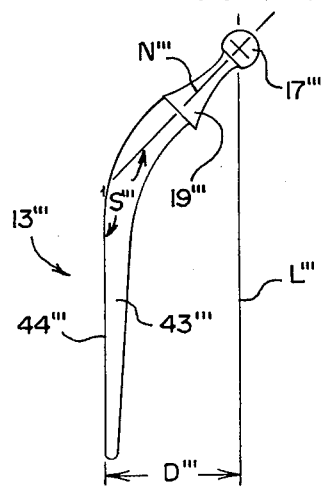

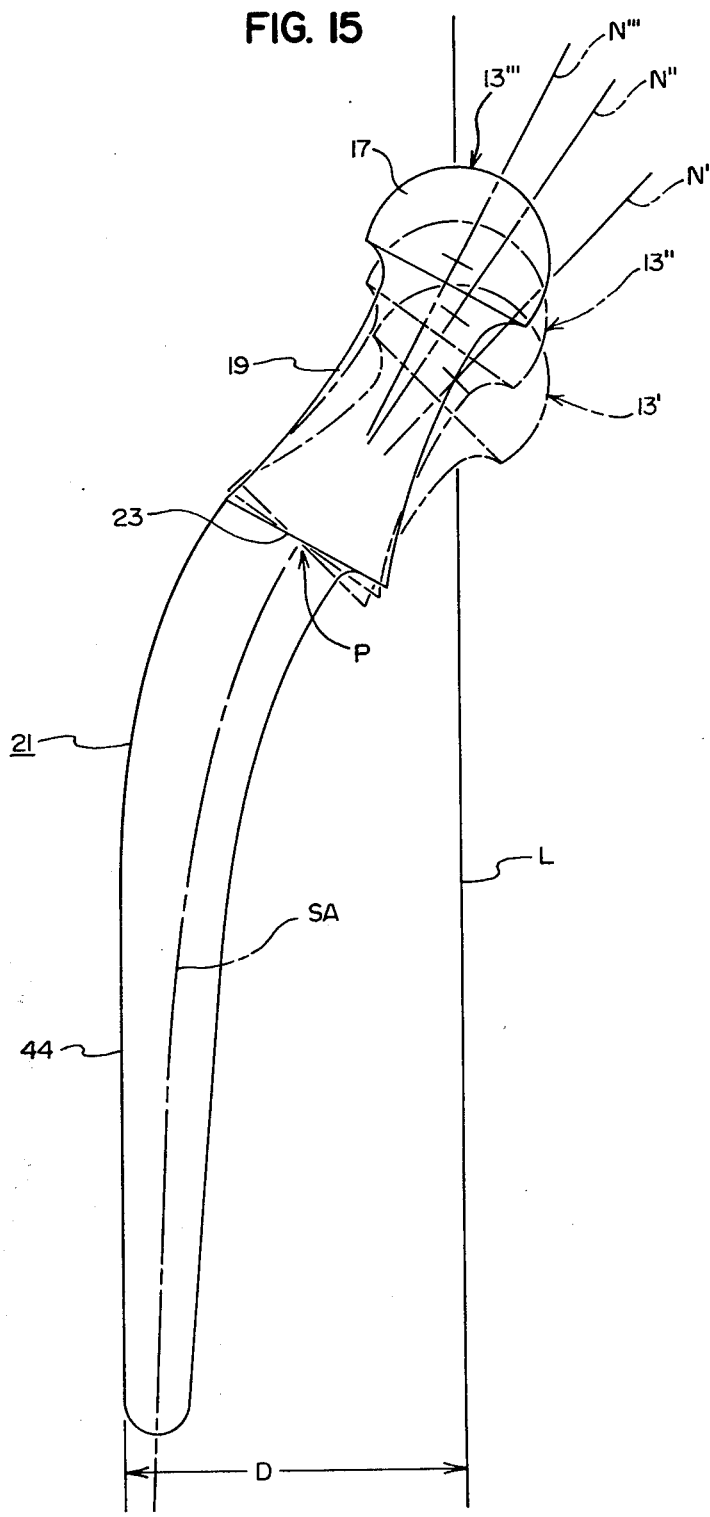

HIP JOINT PROSTHESIS

CROSS-REFERENCE TO RELATED APPLICATION

This is a continuation of our application, Ser. No. 768,604, filed Feb. 14, 1977, entitled "Hip Joint Prosthesis", now abandoned.

BACKGROUND OF THE INVENTION

1. Field of the Invention

This invention relates to the field of prostheses for use in the replacement of at least a portion of a defective hip joint.

2. Description of the Prior Art

In the use of prostheses for the replacement of hip joints there have been problems of failures in these hip systems. There are tremendous forces exerted on the prostheses and the related bone structures during activity of the patient. Thus, in jumping from a 2-3 foot elevated surface to a lower surface the loads placed on the hip joint can, for example, be many times the body weight, and for higher elevations the load factors will be greatly multiplied. The abovementioned failures can occur in the breakdown of the bone, in the cement, and in the femoral prosthesis itself.

Before the introduction of the use of cement in the hip systems many different femoral component designs were utilized, and with the advent of the use of cement in such systems the femoral component, having sharp edges, would cut into the cement, causing cracking and other problems. Also, such prior devices had depressions or undercut portions, which when the cement hardened would lock the femoral prosthesis in place against removal so that it for some reason another operation were necessary to remove the prosthesis and replace it, then it would be difficult for the prosthesis to be removed.

A major disadvantage of the femoral components of prior hip joint prostheses occurs when, after the surgeon has prepared the femur to receive a certain normal-size femoral component (i.e., normal for the particular size and bone structure of the patient) by reaming and broaching the shaft of the femur, he discovers by trial and error or the like that the use of that specific femoral component will result in a hip joint that is too tight or too loose. This may be due to the abnormal structure of the patient's hip joint and surrounding bone structure, the deterioration that has occured to the patient's hip joint, or the like. The prior femoral components were adapted in two known ways to adjust the tightness of the hip joint. First, some prior femoral components are made with neck portions of different lengths while maintaining the same shape and size of stem and head and the same angle between the neck portion and the stem. While the use of such components does result in varying the tightness of the hip joint, it also causes the shaft of the femur to be displaced from the normal position as provided by a normal healthy hip joint which results in more stress on the hip joint and surrounding areas, and the like. Second, some prior femoral components are made with stems of different curvatures to thereby vary the angle between the shaft and the neck portion while maintaining the same length neck portion and same size head. While the use of such components does result in varying the tightness of the hip joint, it also requires the surgeon to reprepare the femur to receive the specific curvature of the stem of the proper component which results in lengthening the time required to complete the operation thereby causing the patient more trauma and the like, often results in weakening the shaft of the femur since more bone is removed than would have been absolutely necessary if the curvature of the stem had not changed, and also results in displacing the shaft of the femur from the normal position as provided by a normal healthy hip joint.

Some of the prior art devices are shown in the following U.S. Pat. Nos.: 3,918,102; 3,965,490; 3,922,726; 3,863,273, and D-235,485. Also, there is a prior device known as the "Charnley Total Hip" which has a stem portion that is flat on the posterior and anterior surfaces, is substantially uniform in thickness as measured in the A-P (anterior-posterior) direction, and has a neck portion circular in cross-section. Also, among the prior art devices is total hip system known by the trademark "Protasul". None of the above prosthetic devices disclose, teach or suggest the present invention.

SUMMARY OF THE INVENTION

The present invention is directed toward overcoming the heretofore mentioned and other problems by providing a highly effective hip joint prosthesis, in which:

1. The stem of the femoral component has a smooth uninterrupted outer surface without any depressions and is continuously tapered from the proximal end to the distal end thereof in both the medial-lateral and anterior-posterior planes. This characteristic of the stem provides distribution of the load along the entire length of the stem, and provides wedging means for forcing the cement into the crevices of the bone when the prosthesis is put into place, and provides for easy removal of the stem in the event of a revision procedure. Thus, there is a firm support with the stem being locked tight against any undesired movement during use, yet is not locked into the cement against removal in the event of a revision procedure in which it is necessary to remove the stem.

2. The stem of the femoral component in cross-section is oval shaped with the shorter axis of the oval being oriented in an anterior-posterior plane, and the longer axis of the oval being oriented in the lateral-media plane so that an increased amount of material is provided in the lateral-medial plane where the stress during weight bearing movements of the leg is highest.

3. The outer surface of the stem is smooth and has rounded corners so that there is no cracking or cutting into the cement.

4. The neck portion in cross-sectional dimensions is narrower in its anterior-posterior dimension than in its lateralmedial dimension so that in the lateral-medial direction which takes the greatest load there is increased material, yet in the anterior-posterior dimension the material is decreased so that greater forward and rearward motion of the neck of the prosthesis is obtained and therefore of the leg of the patient in the forward and rearward direction.

5. The acetabular component includes a substantially hemispherical body which has a constant thickness from the socket thereof outwardly to the exterior surface whereby there is longer wear life of the acetabular component as compared with previous devices in which grooves were cut into the body portion. Also, the acetabular component does not overhang the head but is substantially flush therewith whereby there is greater movement of the femoral component relative to the acetabular component.

6. For the different sizes of femoral components a relationship has been established between the lengthened neck portion and the angle of the neck so that the leg or femur is kept in a straight position under the hip for better weight bearing.

7. The length of the neck portion of the femoral component may be varied without changing the distance between the center of the head and the longitudinal axis of the stem and without changing the curvature of the stem. This results in allowing the surgeon to substitute different femoral components having different length neck portions to vary the tightness of the hip joint without causing the shaft of the femur to be displaced and without being required to re-prepare the femur.

8. The longitudinal axis of the neck portion of the femoral component may be displaced relative to the longitudinal axis of the stem by an amount proportional to the length of the neck portion so as to maintain the alignment of the femur with the pelvis substantially the same as a normal healthy hip joint.

DESCRIPTION OF THE DRAWINGS

FIG. 1 is a front elevational view of the hip prosthesis of the present invention.

FIG. 2 is a top elevational view thereof.

FIG. 3 is a sectional view taken as on line III—III of FIG. 1.

FIG. 4 is a sectional view taken as on line IV—IV of FIG. 1.

FIG. 5 is a sectional view taken as on line V—V of FIG. 1.

FIG. 6 is a sectional view taken as on line VI—VI of FIG. 1.

FIG. 7 is a sectional view taken as on line VII—VII of FIG. 1.

FIG. 8 is a partially sectionalized view showing the hip prosthesis of the present invention implanted in the hip and femur.

FIG. 9 is an elevational view of the acetabular component of the present invention.

FIG. 10 is a top view thereof.

FIG. 11 is a sectional view taken as on line XI—XI of FIG. 10.

FIGS. 12, 13 and 14 are front elevational views showing the relationship of certain lengths, distances and angles of three sizes of the femoral components of the present invention.

FIG. 15 is a diagramatic view showing in solid lines a front elevational view of a femoral component having a certain length neck portion and showing in broken lines the relation thereto of femoral components having different length neck portions.

DESCRIPTION OF THE PREFERRED EMBODIMENT

Referring now to the drawings, the prosthetic hip joint 11 of the present invention includes a femoral component 13 for implanting in the medullary canal M of the femur F by cement C, and an acetabular component 15 for implanting in the acetabulum A with cement C.

The femoral component 13 includes a head 17, a neck portion 19, a stem 21, and a shoulder 23 adjacent the juncture of neck portion 19 and stem 21. Femoral component 13 is preferably integrally formed of a suitable rigid bio-compatible material, as chromecobalt or stainless steel, with head 17 being rigidly joined to one end of neck portion 19 and the other end of neck portion 19 being rigidly joined to the proximal end 25 of stem 21. Shoulder 23 is provided at the end of neck portion 19 adjacent its juncture with stem 21.

Head 17 has an outer surface with a major portion thereof as at 29 being spherical for fitting into the socket 31 of the acetabular component 15, as shown in FIG. 8. Head 17 is preferably flat along the bottom side 33 surrounding the juncture of head 17 with neck 19 and with a radius 33' being provided at the juncture.

Neck portion 19 has a smooth outer surface and, in cross-section, is elliptical with the narrower portion or shorter axis of the ellipse extending in an anterior-posterior direction (shown by the line A-P) and with the wider portion or longer axis of the ellipse extending in a lateral-medial direction (shown by the line L-M). It should be noted that the term "anterior-posterior" and "lateral-medial" directions are determined by the orientation of the femoral component 13 relative to the body of the patient when implanted therein, that is, the anterior-posterior direction extends fore and aft relative to the body and lateral-medial extends sidewise relative to the body. From the foregoing, it will be seen that more metal in the stem 21 is provided in the lateral-medial direction or plane where the load forces are greatest and at the same time the neck portion 19 is thinner in the anterior-posterior direction or plane so that there is less interference with the acetabular component 15, thereby giving a greater range of fore and aft movement of the femoral component 13 and femur F. It will be noted that neck 19 is narrower in the area 37 just below the juncture with head 17 and flares outwardly to its termination where shoulder 23 is provided on the end of the neck portion 19 adjacent the juncture with stem 21. The shoulder 23 overhangs the proximal end 25 of stem 21 on the anterior, posterior and medial sides thereof, and the lateral edge of the neck portion 19 is substantially flush with the lateral portion of the proximal end 25 of stem 21.

Stem 21, when viewed from the front, as in FIG. 1, is curved and is thicker in the proximal portion 41 than in the straight distal portion 43. As viewed from the top, as in FIG. 2, stem 21 is substantially straight.

One of the important features of the present invention is the configuration of the stem 21. It has a smooth uninterrupted outer surface 45 without any depressions and is continuously tapered from the proximal end 25 to the distal end 47 in both the anterior-posterior and lateral-medial dimensions or planes. Thus, the stem 21 in cross section is oval shaped with the oval becoming increasingly smaller from the proximal end 25 to the distal end 47, as is shown by the representative sections of the stem in FIGS. 4, 5, 6 and 7. The longer dimensions or axes of the ovals are disposed along the lateral-medial direction or plane, as shown as at L-M, and the shorter dimensions or axes of the ovals are disposed along the anterior-posterior direction or plane. It will be noted that the corners are rounded and there are no sharp corners, which would otherwise cut into the cement and cause cracking or cutting of the cement. Also, this particular configuration of stem 21 produces synergistic results which will be understood more fully in the description to follow of the use of the prosthetic hip joint 11.

There are preferably at least three sizes of femoral components 13, and they are so arranged that there is anatomical compatibility and yet there is a minimization of the concentration of stresses in the femoral components, with improved distribution of weight bearing and increased range of motion. FIGS. 12, 13, 14 and 15 show how the sizes are preferably related. FIG. 12 is the component with the smaller size neck portion, FIG. 13 with the medium size, and FIG. 14 the one with the longer neck portion. FIG. 15 shows the three components superimposed upon one another. For clarity's sake, the component with the shorter length neck portion and its parts has been designated by the prime mark (e.g., 13′), the middle size by a double prime mark (e.g., 13″) and the longer size by a triple prime mark (e.g., 13‴). It will be noted that the respective distances D′, D″, D‴ between lines L′, L″, L‴ through the centers of the heads 17′, 17″, 17‴ and parallel with lateral edges 44′, 44″, 44‴ of the straight portions 43′, 43″, and 43‴ are the same on all of the sizes, and to provide for different neck dimensions the angles S′, S″ and S‴ between the neck axes N′, N″ and N‴ and the lateral edges 44′, 44″, and 44‴ of straight portions 43′, 43″, and 43‴ are different. Thus, when the length of the neck portion 19 is varied for any reason apparent to those skilled in the art such as to vary the tightness of the hip joint, the distance between the longitudinal axis of the stem 21 or the lateral edge 44 thereof and the center of the head 17 remains constant and unchanged as clearly indicated by the distance D between the lateral edge 44 of the stem 21 and the line L passing through the center of the head 17 in FIG. 15. Also, FIG. 15 clearly shows that the size, shape and curvature of the stem 21 remains the same for the different lengths of the neck portion 17 of the three femoral components 13′, 13″, 13‴. The size and shape of the head 17 also remains the same. This is accomplished by, in effect, sliding and rotating the neck portion 19 about an imaginary point P on the shoulder 23 (see FIG. 15) when the length of the neck portion 19 is varied to maintain the center of the head 17 substantially aligned with the line L without changing the shape, size or curvature of the stem 21. It should be noted that the pivot P moves along the shoulder 23. The longitudinal axis of the neck portion 19 is preferably displaced relative to the longitudinal axis SA of the stem 21 an amount proportional to the length of the neck portion 19 so as to maintain the alignment of the femur with the pelvis substantially the same as would result if the hip joint were normal and healthy. More specifically, the longitudinal axis of the neck portion 19 is displaced outwardly relative to the longitudinal axis SA of the stem 21 a greater amount as the length of the neck portion 19 is increased as shown clearly in FIG. 15 with the axes of the neck portions 19 of the three femoral components 13 identified as N′, N″ and N‴. Such a system of femoral components 13 allows a surgeon to prepare the femur F to receive a stem 21 of a certain size femoral component 13 and the, if it later appears that the hip joint will be too loose or too tight if that certain size femoral component 13 is used, he can replace that femoral component 13 with one that has a longer or shorter neck portion 19 without causing the shaft of the femur F to be displaced outwardly or inwardly relative to the position it would have taken if the specific femoral component 13 which the femur F was prepared to receive had been implanted (that is, the femur F will maintain substantially the same alignment relative to the pelvis as it would have if the hip joint was normal and healthy, regardless of which length neck portion 21 is used), and without having to re-prepare the femur F to receive a different size, shape or curvature of the stem 21. The specific dimensions of the three sizes having the 25mm. head are preferably as follows:

|  | Neck Length* | Neck Angle |
|---|---|---|
| Component 13′ | 1.75″ | 135° |
| Component 13″ | 2.00″ | 144° |
| Component 13‴ | 2.25″ | 149.7° |

*Neck length as measured from top of head to bottom of neck.

Also, other size heads are preferably provided, for example, 32mm., which would have different neck lengths. In addition, it will be apparent to those skilled in the art that the femoral component system of the present invention may consist of different sets of femoral components 13, each set having stems 21 of different sizes, shapes and curvatures. For example, the present invention may include a first set of three femoral components 13, each having neck portions 19 of different lengths and each having a large, straight stem 21. Likewise, the present invention may include a second set of three femoral components 13, each having neck portions 19 of different lengths and each having a small, curved stem 21.

The acetabular or cup component 15 is preferably integrally formed from a suitable plastic material, as ultra-high molecular weight polyethylene. Acetabular component 15 includes a substantially hemispherical body 55 with the inner surface thereof being defined by socket 31 and having an exterior surface 57 spaced outwardly from socket 31. One of the important features of the acetabular component 15 is that body 55 is of a constant thickness from socket 31 to exterior surface 57 so that there is a uniform wear thickness or portion which is not thin in areas such as with some of the previous acetabular cups in which cement grooves were formed in the exterior surface extending towards the socket to reduce the thickness of the body in these areas, and with rings being provided between these grooves. In contrast, with acetabular component 15 there are no depressed grooves into the body 55 but rather there are a plurality of rings 59 integrally attached to and projecting outwardly from the exterior surface 57 of body 55 and spaced apart to define cement receiving grooves 61 therebetween.

Acetabular component 15 includes an entrance opening 63 which opens into socket 31. An annular base portion 65 of acetabular component 15 surrrounds entrance opening 63 and is integrally joined with body 55 and terminates in an annular surface 67. Notches 69 are provided in rings 59 and annular base portion 65, and are spaced around the rings 59 and the base portion 65.

In implanting the prosthetic hip joint 11, surgical procedures well known to those skilled in the art are utilized to implant the acetabular component 15 and the acetabulum A and the femoral component 13 in the femur F utilizing cement C. There are several synergistic results which are provided by the present invention, particularly in connection with the structure and configuration of the components of the present invention. These results include among others, the wedging or forcing outwardly of the cement into the cavities of the bone when the stem 21 is inserted into the medullary canal M of the femur F due to the stem being continously tapered from the proximal end to the distal end. Also, due to this wedging action when the cement is hardened, the stem 21 is held firmly against wobbling, there is an even distribution of the load along the entire length of the stem rather than concentrating in one area that would place stress upon the area and cause possible fracture of the stem, and yet the continuous taper permits easy removal of the stem later on if necessary as for example in a revision procedure. In addition, due to the angular relationship heretofore mentioned with the increased length of the neck portion anatomical compatibility is provided at an improved level of femoral support. Further, as heretofore pointed out, by varying the length of the neck portion 19 of the femoral component 13 without changing the distance between the longitudinal axis of the stem 21 and the center of the head 17 and without changing the curvature and shape of the stem 21, the present invention allows the tightness of a hip joint to be varied after the femur F has been prepared to receive a specific stem 21 without changing the normal displacement of the shaft of the femur F and without requiring the femur F to be re-prepared to receive a different stem 21. Also, other advantages which have heretofore been pointed out are provided.

Although the invention has been described and illustrated with respect to a preferred embodiment thereof, it is to be understood it is not to be so limited since changes and modifications may be made therein which are within the full intended scope of the invention.

We claim:

1. A prosthetic hip joint for use in the replacement of a defective hip joint, said prosthetic joint comprising:
    a. an acetabular component for implanting in the acetabulum, said acetabular component being formed of plastic and being provided with a socket; and
    b. a femoral component including:
        1. a head movably received in said socket,
        2. a stem for implanting in the femoral canal, said stem having proximal and distal ends, said stem having an uninterrupted outer surface and being continuously tapered from said proximal end to said distal end, and
        3. a neck portion being rigidly joined at one end thereof to said stem at said proximal end of said stem and rigidly joined at the other end thereof to said head, said neck portion being elliptical in cross-section with the narrower portion or shorter axis of the ellipse extending in an anterior-posterior direction and with the wider portion or longer axis of the ellipse extending in a lateral-medial direction.

2. A prosthetic hip joint as set forth in claim 1 wherein said stem is oval shaped in cross section with the longer axis of the oval when the stem is implanted in a femoral canal being oriented in a lateral-medial plane and the shorter axis in an anterior-posterior plane, and said stem being tapered as considered relative to both the lateral-medial direction and the anterior-posterior direction.

3. A prosthesis hip joint as set forth in claim 2 wherein the outer surface of said neck portion are smooth.

4. A prosthesis hip joint as set forth in claim 1 wherein said outer surface is smooth and rounded.

5. A hip prosthesis hip joint as set forth in claim 1 wherein said acetabular component includes a substantially hemispherical body with the inner surface thereof being defined by said socket and having an exterior surface spaced outwardly from said socket, said body having a constant thickness from said socket outwardly to said exterior surface, and a plurality of rings projecting outwardly from said exterior surface and being spaced apart to define cement receiving grooves therebetween.

6. A prosthesis hip joint as set forth in claim 5 wherein said head is substantially flat on the end thereof that is joined to said neck portion, and said acetabular component includes an entrance opening to said socket and said acetabular component includes an annular base portion surrounding said entrance opening, integrally joined with said body, and terminating in an annular surface; said flat side of said head being movable to a position substantially flush with said annular surface.

7. A prosthetic hip joint for use in the replacement of a defective hip joint, said prosthetic joint comprising:
    a. an acetabular component for implanting in the acetabulum, said acetabular component being formed of plastic and being provided with a socket, said acetabular component including a substantially hemispherical body with the inner surface thereof being defined by said socket and having an exterior surface spaced outwardly from said socket, said body having a constant thickness from said socket outwardly to said exterior surface, and a plurality of rings projecting outwardly from said exterior surface and being spaced apart to define cement receiving grooves therebetween; and
    b. a femoral component including:
        1. a head removably received in said socket,
        2. a stem for implanting in the femoral canal, said stem having proximal and distal ends, said stem having an uninterrupted outer surface and being continuously tapered from said proximal end to said distal end, said outer surface being smooth and rounded, said stem being oval shaped in cross-section with the longer axis of the oval when the stem is implanted in a femoral canal being oriented in a lateral-medial plane and the shorter axis in an anterior-posterior plane, said stem being tapered as considered relative to both the lateral-medial direction and the anterior-posterior direction,
        3. a neck portion being rigidly joined at one end thereof to said stem at said proximal end of said stem to provide a shoulder at the juncture with said stem and rigidly joined at the other end thereof to said head, said neck portion being elliptical in cross-sectional dimensions and being narrower in its anterior-posterior dimension than in its lateral-medial plane.

8. A prosthetic hip joint femoral component comprising:
    a. a head for movable reception in a socket,
    b. a stem for implanting in the femoral canal, said stem having proximal and distal ends, said stem having an uninterrupted outer surface and being continuously tapered from said proximal end to said distal end, and
    c. a neck portion being rigidly joined at one end thereof to said stem at said proximal end of said stem to provide a shoulder at the juncture of said stem and rigidly joined at the other end thereof to said head, said neck portion being elliptical in cross-section with the narrower portion or shorter axis of the ellipse extending in an anterior-posterior direction and with the wider portion or longer axis of the ellipse extending in a lateral-medial direction.

9. A prosthetic hip joint femoral component as set forth in claim 8 wherein said stem is oval shaped in cross-section with the longer axis of the oval when the stem is implanted in a femoral canal being oriented in a lateral-medial plane and the shorter axis in an anterior-posterior plane, and said stem being tapered as considered relative to both the lateral-medial direction and the anterior-posterior direction.

10. A prosthesis hip joint femoral component as set forth in claim 8 wherein said outer surface is smooth and rounded.

11. A prosthetic hip joint femoral component comprising:
   a. a head for removable reception in a socket,
   b. a stem for implanting in the femoral canal, said stem having proximal and distal ends, said stem having an uninterrupted outer surface and being continuously tapered from said proximal end to said distal end, said outer surface being smooth and rounded, said stem being oval shaped in cross-section with the longer axis of the oval when the stem is implanted in a femoral canal being oriented in a lateral-medial plane and the shorter axis in an anterior-posterior plane, and said stem being tapered as considered relative to both the lateral-medial direction and the anterior-posterior direction,
   c. a neck portion being rigidly joined at one end thereof to said stem at said proximal end of said stem to provide a shoulder juncture with said stem and rigidly joined at the other end thereof to said head, said neck portion being elliptical in cross-sectional dimensions and being narrower in its anterior-posterior dimension than in its lateral-medial dimension.

12. A plurality of prosthetic hip joint femoral components, each of said components comprising:
   a. a head for being movably received in a socket in the pelvis of a hip joint,
   b. a stem for being fixedly implanted in the femoral canal of the femur of a hip joint, and
   c. a neck portion for rigidly joining said head and said stem, the longitudinal axis of said neck portion being displaced relative to the longitudinal axis of said stem an amount proportional to the length of said neck portion so as to maintain the alignment of the femur with the pelvis substantially the same as a normal healthy hip joint, said head and stem of each of said components being substantially the same shape and size, said neck portion of each of said components being of a different length, the longitudinal axis of said neck portions being displaced outwardly relative to the longitudinal axis of said stems a greater amount as the length of said neck is increased.

13. An improved set of prosthetic hip joint femoral components of the type including a head for being movably received in a socket in the pelvis of a hip joint, including a stem for being fixedly implanted in the femoral canal of the femur of a hip joint, and including a neck portion for rigidly joining said head and said stem, wherein the improvement comprises: said neck portion of each of said components being of a different length with the distance between the center of said head and the longitudinal axis of said stem of each of said components being the same while retaining the same curvature for each stem and the same shape and size for each head and stem for each of said components.

14. A system for use in replacing at least a portion of a hip joint, said system comprising: a plurality of prosthetic femoral components of the type including a head for selectively replacing the head of the femur of a hip joint and for selectively being movably received in a socket in the pelvis of a hip joint, including a stem for being selectively fixedly implanted in the femoral canal of the femur of a hip joint, and including a neck portion for rigidly joining said head and said stem; said neck portion of each of said plurality of femoral components being of a different length; the distance between the center of said head and a line aligned with one lateral edge of said stem and the curvature of said stem being the same for each of said plurality of femoral components.

* * * * *